United States Patent [19]

Kitchen

[11] Patent Number: 4,559,812
[45] Date of Patent: Dec. 24, 1985

[54] RHEOMETER AND METHOD OF USE THEREOF

[75] Inventor: Terence J. Kitchen, Surrey, England

[73] Assignee: SPRI Limited, Doking, England

[21] Appl. No.: 618,856

[22] Filed: Jun. 8, 1984

[30] Foreign Application Priority Data

Jul. 15, 1983 [GB] United Kingdom ............... 8319195

[51] Int. Cl.$^4$ ........................................... G01N 11/14
[52] U.S. Cl. ........................................ 73/59; 73/843; 374/47
[58] Field of Search ............... 73/59, 60, 843; 374/47, 374/48, 46

[56] References Cited

U.S. PATENT DOCUMENTS

| 3,182,494 | 5/1965 | Beatty et al. | 374/48 |
| 3,535,914 | 10/1970 | Veith et al. | 374/46 |
| 3,688,568 | 9/1972 | Karper et al. | 374/47 |
| 3,769,830 | 11/1973 | Porter et al. | 374/48 |
| 4,275,600 | 6/1981 | Turner et al. | 374/46 X |

OTHER PUBLICATIONS

Berezhnaya, G. V. et al., Rheogoniometer for Measurements of Viscoelastic Properties of Polymeric Systems In Institute of Petrochemical Synthesis, vol. 38, No. 11, pp. 1403–1405, Nov. 1972.

*Primary Examiner*—Stewart J. Levy
*Assistant Examiner*—Joseph W. Roskos
*Attorney, Agent, or Firm*—Sughrue, Mion, Zinn, Macpeak and Seas

[57] ABSTRACT

A rheometer of the type which includes a chamber (26) in which, in use, a sample of rubber or of a synthetic elastomer which is to be tested is held under pressure in contact with a rotor (27), and means for measuring torque applied to the rotor (27) as it is rotated in contact with the sample, is provided with a driving mechanism (35) for rotating the rotor (27) driven by two pulse-operated electric stepping motors (40, 41) operating through pinions (44, 49) and a differential gear (46). The use of two stepping motors (40, 41) and the differential gear (46) enables the rheometer to test the sample in various ways. Firstly the rotor (27) may be rotated in one direction to strain the sample beyond its maximum recovery and then be rotated in a reverse direction step by step until there is zero torque on the rotor and the total reverse rotation then indicates the total angular recovery of the sample. Alternatively the rotor may be rotated continuously in one direction and the varying torque upon it may be measured as the sample is vulcanized or cured as is done with a Mooney Viscometer. As another alternative, the rotor (27) may be oscillated by varying the speeds of the motors (40, 41) without stopping the motors and this provides test results similar to those produced by a rheometer of the oscillating disc type.

12 Claims, 7 Drawing Figures

RHEOMETER AND METHOD OF USE THEREOF

This invention relates to rheometers, which are instruments for measuring physical properties of uncured or unvulcanised, or partly cured or partly vulcanised, rubber or synthetic elastomers.

The invention is specifically concerned with rheometers which include a chamber in which, in use, a sample of the material of which the properties are to be measured is held under pressure, a rotor which has a surface in contact with the sample in the chamber and has a drive by which it is rotatable, and torque measuring means for measuring the torque applied to the rotor as it is rotated. The rotor may be a disc which is rotatably mounted in the chamber and, in use, is entirely surrounded by the sample of material, or it may alternatively form a part of the wall of the chamber, the remainder of the wall of which is stationary. such rheometers are subsequently referred to as being of the type described.

One of the physical properties of rubber or synthethic elastomers which is measured by rheometers of the type described is the recovery of the material which takes place after it has been subjected to a substantial shearing strain.

An early rheometer of the type described, developments of which are still commonly used today, is known as the Mooney Viscometer and is described in U.S. Pat. No. 2,037,529. In this instrument, the rotor is turned slowly in one direction and the torque required to turn it is constantly measured as the material is cured or vulcanised. This instrument can only be used to measure characteristics during the early stages of curing or vulcanisation because as the material stiffens the resistance to continuous rotation of the rotor is such that excessive heat is generated.

In a later instrument, as described in GB-A No. 1036904, the rotor is oscillated and again the torque required to move the rotor is measured against time as curing or vulcanisation proceeds.

In the first of these instruments, the rotor can be disconnected from its drive at any time during the measurement and the magnitude of the angular return movement of the rotor, which is brought about by the recovery of the material in the chamber, is then measured.

It is, however, difficult to measure the angular movement very accurately and in any case this measurement requires the rheometer to incorporate an angular deflection measuring device in addition to the torque measuring means. What is more, it is only practicable to measure the total angular recovery of the material in the chamber and, if required, the time taken after the drive has been disconnected for this total recovery to take place.

In the second of these instruments, the rotor cannot be disconected from its oscillating drive and therefore measurements of the recovery of the material cannot be made.

The aim of the present invention is to enable more accurate and informative measurements of the recovery of samples of rubber or synthetic elastomers to be made during the course of vulcanisation or curing by means of a rheometer of the type described.

To this end, according to one aspect of this invention, a rheometer of the type described is characterised in that the drive is reversible and includes a pulse-operated electric stepping motor which is connected to the rotor through gearing, the drive enabling the rotor to be rotated selectively in either direction in steps of not more than 20 minutes of arc.

The construction of the rotor drive in this way also gives rise to a new method of measuring the recovery of a sample of rubber or of a synthetic elastomer after it has been subjected to a substantial shearing strain using a rheometer in accordance with the invention just described.

This method, in accordance with another aspect of the present invention, comprises inserting a sample of the material under pressure into the chamber of the rheometer in accordance with the invention and rotating the rotor in one direction to apply a substantial shear strain to the sample, the angular strain being greater than the maximum angular recovery of the sample, and the method is characterised in that the rotation of the rotor in the one direction is then stopped; the rotor is rotated in a reverse direction step by step through predetermined angles; the torque applied to the rotor by the sample as it recovers after each step of the reverse rotation is observed from the torque measuring means, and then the rotor is rotated through a further step until the observed torque falls to zero, at which time the reverse rotation of the rotor indicates the angular recovery of the sample.

By the use of this method, which is made possible by the construction of the drive of the rheometer in accordance with the invention, it is possible to obtain a much more accurate measurement of the recovery of the sample than is possible with conventional rheometers of the type described. This is because the total rotation of the rotor in the reverse direction is directly indicated by the total number of pulses delivered to the stepping motor to cause it to rotate in the reverse direction. The number of pulses can be exactly measured whereas, as already mentioned, angular deflection measuring instruments are not always very accurate.

It has been found that steps of 20 minutes of arc are the maximum through which the rotor can be rotated to provide a reading of the recovery of the sample of sufficient accuracy for practical purposes, but preferably the construction of the stepping motor and of the gearing through which the rotor is connected to the stepping motor are such that each step is smaller than this and, in one example, each step is 1.8 minutes of arc and in another example, where very great accuracy is necessary, each step of rotation is only through a few seconds of arc.

As each step of rotation in the reverse direction takes place, this rotation will be assisted by a torque exerted on the rotor by the sample as it recovers. As the sample moves towards the limit of its recovery, however, the assisting torque will decrease. Rotation continues step by step until, as already described, after a step of reverse rotation, the torque on the rotor in the direction of reverse rotation falls to zero. It is this that indicates that the full angular recovery of the sample has taken place and the magnitude of the angle of recovery is then equal to the total rotation of the rotor through all the steps in the reverse direction.

Preferably the time taken after each step of reverse rotation for the torque to increase to its maximum in the reverse direction is measured. For this purpose the rheometer in accordance with the invention is preferably provided with a timing device which, in operation, indicates the time taken for variations in the torque on the rotor to take place after the rotor has been rotated by the drive. For this purpose, the timing device is preferably electrical and so also is the torque measuring means. The torque measuring means and the timing device are both connected to an electronic controller which indicates the required time intervals automatically. The same electronic controller preferably also includes pulse generating circuits for operating the electric stepping motor, or the motors if the drive includes more than one.

The relationship between the angle of recovery of the sample and the time taken for this recovery to take place can give valuable information about the sample which cannot be obtained by the conventional rheometers of the type described in which only the total angle of recovery is measured.

Preferably, in the method in accordance with the invention, after the last step of reverse rotation of the rotor has taken place and the observed torque has fallen to zero, the rotor is again rotated in a forward direction through one or more steps until a minimum observable torque in the reverse direction is indicated by the torque measuring means.

This final very small forward rotation of the rotor takes up any lag that there may be in the reading of the torque measuring means and also any backlash that there may be in the driving mechanism. In this way a still more accurate measurement of the recovery of the sample may be obtained.

For simplicity, the drive of the rotor may include only a single pulse-operated electric stepping motor which is reversible. To increase the versatility of the rheometer in accordance with the invention, however, the drive preferably incorporates means by which the rotor may be rotated step by step continuously in one direction or the other, or by which it may be oscillated by being rotated through one or more steps in one direction followed by rotation through one or more steps in an opposite direction. For this purpose the drive preferably includes two pulse-operated electric stepping motors which are connected to the rotor through differential gearing. With this arrangement rotation of one motor while the other motor is stationary rotates the rotor in one direction, rotation of the other motor while the one motor is stationary rotates the motor in an opposite direction and alternate rotation of the two motors oscillates the rotor.

This drive is however even more advantageous if it is operated by changing the speeds of rotation of the two motors whilst continuing to rotate each motor continuously in one direction. Thus, rotation of one motor faster than the other motor rotates the rotor in one direction; rotation of the other motor faster than the one motor rotates the rotor in an opposite direction and alternate rotation of the two motors faster and slower than each other oscillates the rotor. Operation of the drive in this way has the advantage that it is never necessary to stop either of the motors to rotate the rotor in either one direction or the other or to oscillate the rotor and this is beneficial, because the inertia of stepping motors is considerable. A rapid oscillation can be achieved by increasing the speed of one motor while retarding the other end and then retarding the one motor while increasing the speed of the other alternately.

Preferably the motor or the motors and the gearing form a unit having an output shaft connected to the rotor. The unit is freely rotatably mounted, but is prevented from rotaation by the connection to it of a load cell, which forms the torque measuring means and which indicates the reaction torque on the unit when the rotor is being rotated and hence indicates the torque on the rotor.

Preferably the rotor is a disc which is rotatably mounted in a chamber and, in use, is entirely surrounded by the sample of material being tested. In this case, the chamber is preferably enclosed in a housing which is separable into two parts along a plane transverse to the axis of rotation of the rotor and the part of the housing on the side of the plane remote from the drive has a mechanism by which it can be clamped to the other part of the housing and by which it is movable linearly away from the plane and is tiltable to provide access to the chamber and to the rotor for the insertion and removable of the sample of material into and from the chamber.

An example of a rheometer and of a modification thereof, and an example of a method, in accordance with the invention will now be described with reference to the accompanying somewhat diagramatic drawings in which.

Figure 1:
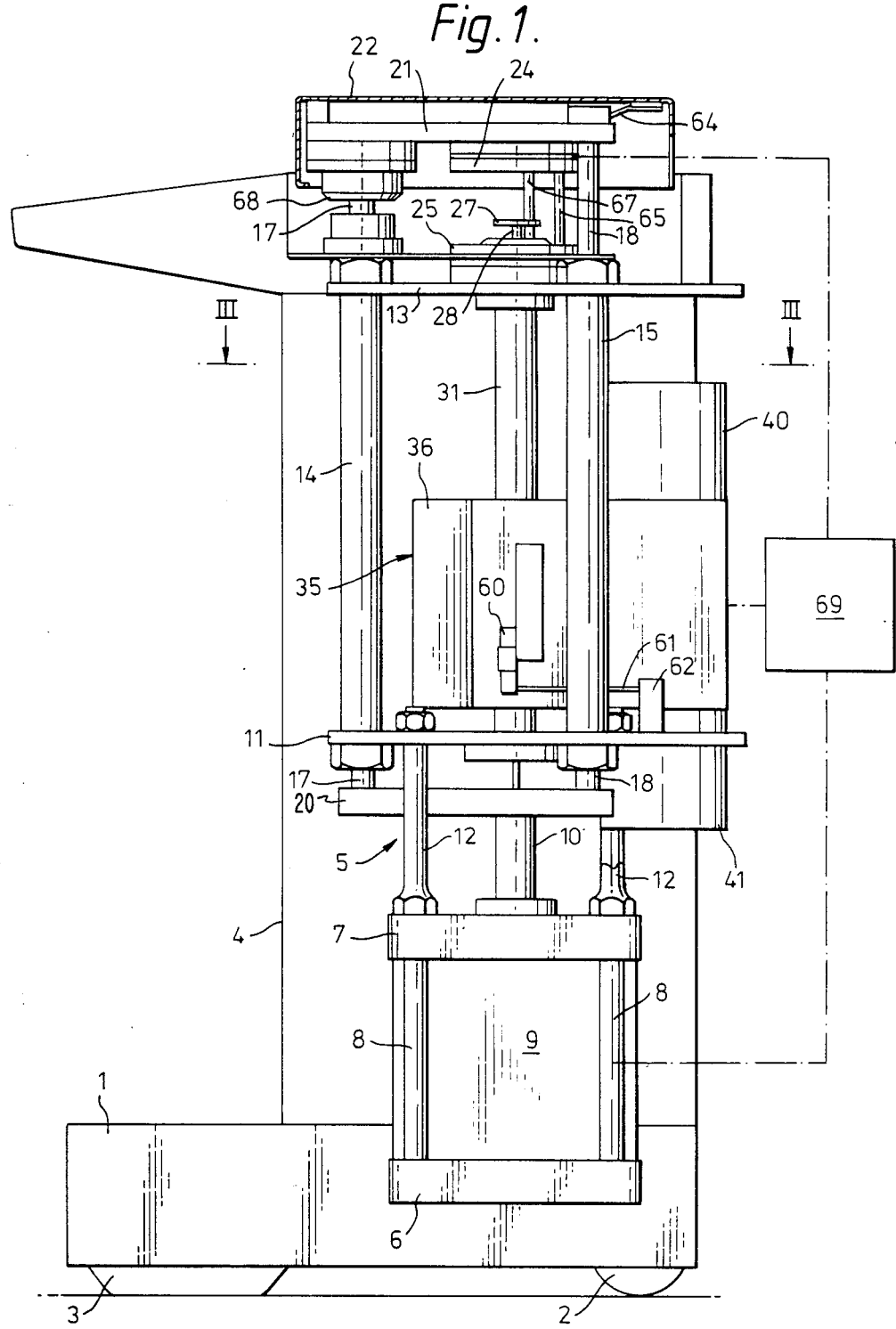
FIG. 1 is a side elevation of the example of the rheometer.

The rheometer has a base 1 which is mounted on a pair of wheels, one of which is shown at 2 and on a foot 3 to enable it to be tipped up onto the wheels 2 and moved about if required. The base 1 supports an outer casing 4 which encloses most of the working parts of the rheometer and it also carries a main supporting framework 5.

The supporting framework 5 includes a bottom plate 6 and a plate 7 which are the end plates of a pneumatic cylinder 9 and are fixed to each other by a cylinder wall 8 of the pneumatic cylinder which also has a piston rod 10.

Figure 3:
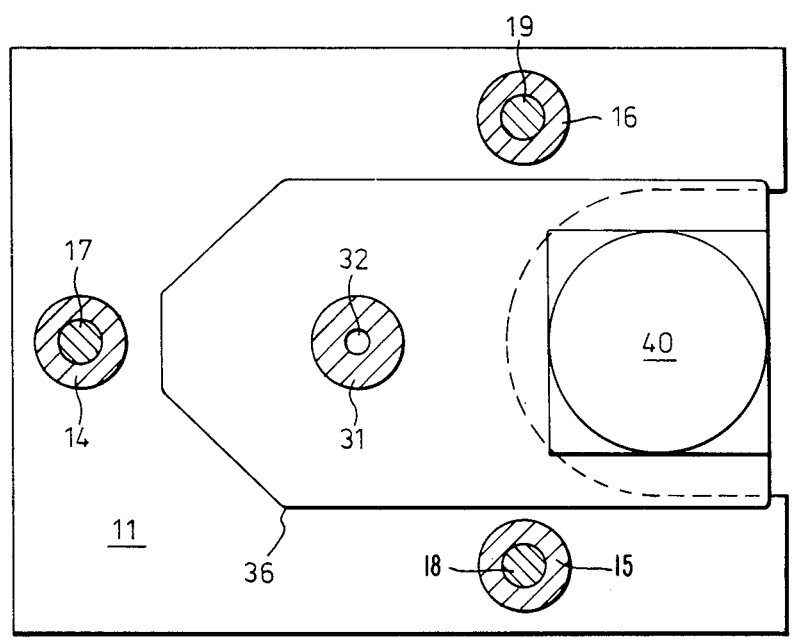
FIG. 3 is a sectional plan as seen in the direction of the arrows on the line III—III in FIG. 1.

Another plate 11 is supported above the plate 7 by columns 12 and yet another plate 13 is fixed above the plate 11 by three tubes 14, 15 and 16, the disposition of which is best shown in FIG. 3.

Three rods 17, 18 and 19 are slidable upwards and downwards in the tubes 14, 15 and 16 respectively and have their lower ends fixed to a cross-head 20 which is itself fixed on the upper end of the piston rod 10 so that the rods 17–19 are movable upwards and downwards by the pneumatic cylinder 9.

Figure 2:
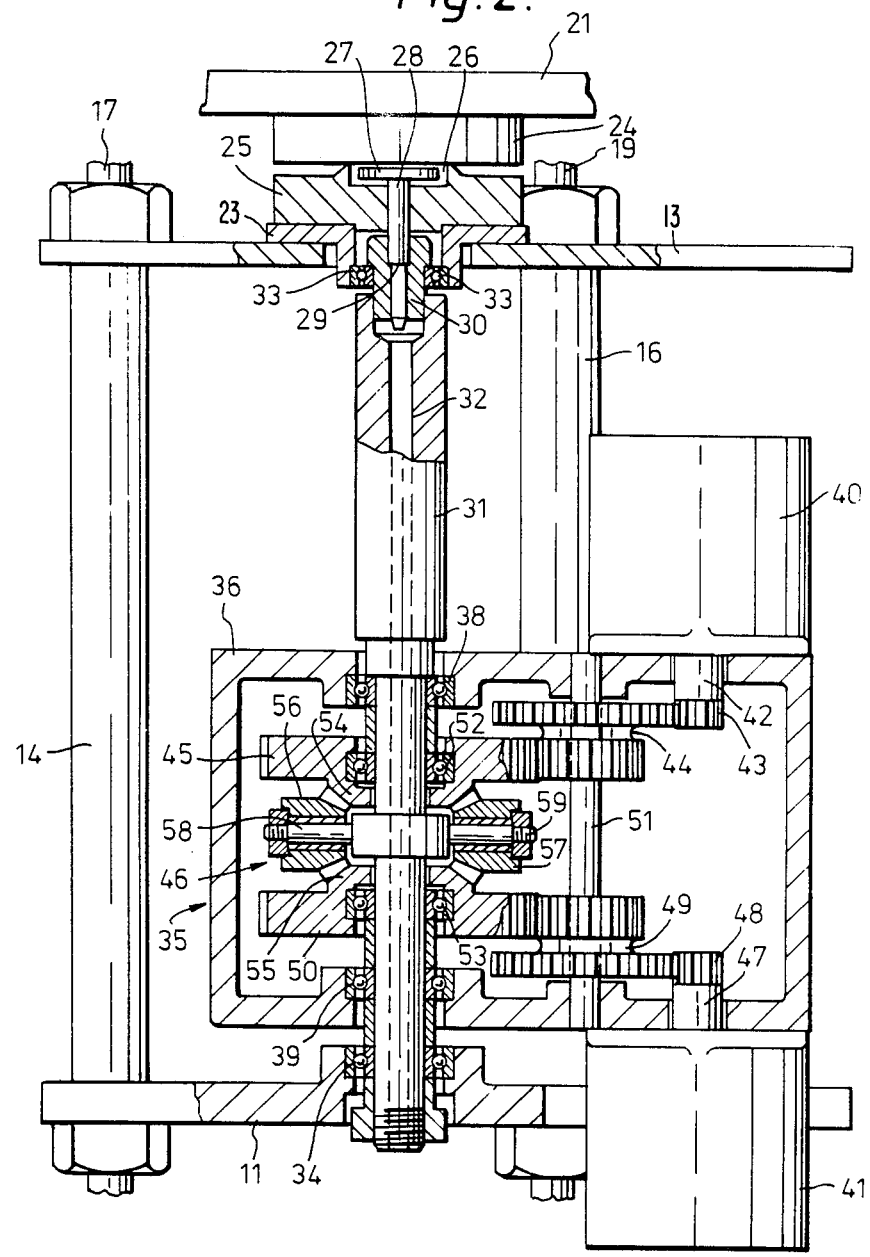
FIG. 2 is a sectional side view of the rheometer to a larger scale and as seen in the same direction as FIG. 1, the section being on a plane extending through the axis of rotation of the rotor of the rheometer.
Figure 4:
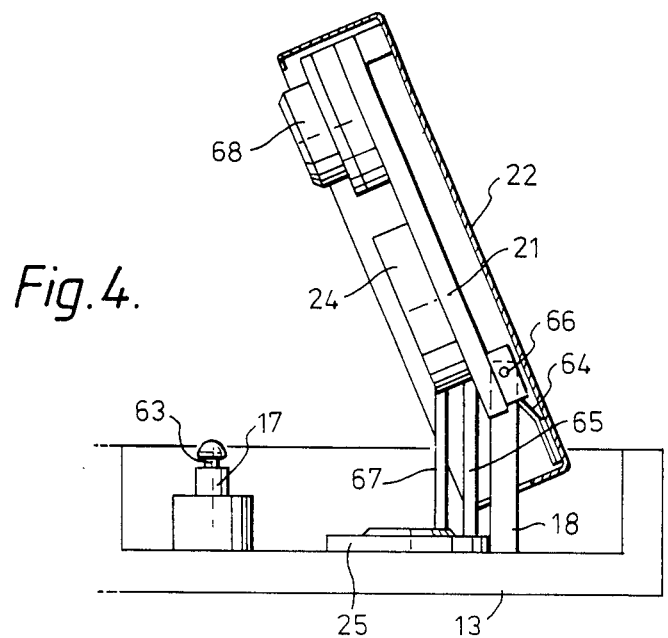
FIG. 4 is a side view of part of the top of the rheometer showing the rotor and the housing, in which in operation the rotor is enclosed, in an open position.
Figure 5:
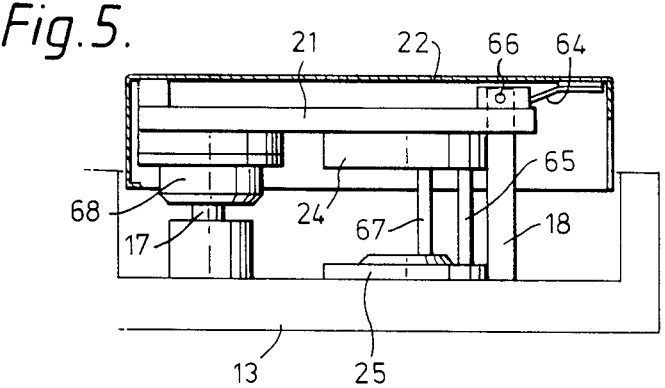
FIG. 5 is a view similar to FIG. 4, but showing the housing in an intermediate position which it passes through during closure of the chamber.
Figure 6:
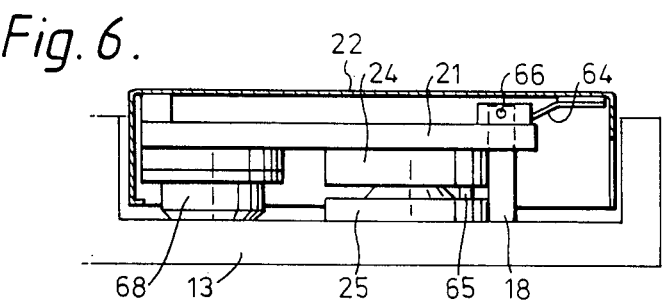
FIG. 6 is a view similar to FIG. 4, but showing the chamber closed.

As shown most clearly in FIGS 4 to 6, an upper platen 21, which lies within an upper cover 22 is pivotally mounted between the upper ends of the rods 18 and 19. A lower platen 23, which is shown most clearly in FIG. 2, is mounted on the plate 13. The upper platen 21 carries an upper die 24 and the lower platen 23 carries a lower die 25. The upper and lower dies 24 and 25 form the two parts of a housing which, when the two dies are closed together as shown in FIGS. 2 and 6, encloses a chamber 26 between them.

The chamber 26 contains a cylindrical disc-like rotor 27 which is mounted on a spindle 28 (see FIG. 2). The spindle 28 has a lower portion 29 of square cross section which fits in a recess of similar cross section in a head 30 which is fixed in a rotor driving shaft 31.

The shaft 31 has a bore 32 and is rotatably mounted in an upper bearing 33 carried in the platen 23 and in a lower bearing 34 carried by the plate 11.

A driving unit 35 for driving the shaft 31 and through it the rotor 27 is rotatably mounted on the shaft 31. The unit 35 comprises a gearbox 36 which is rotatably mounted on the shaft 31 by an upper bearing 38 and a lower bearing 39. The gearbox 36 supports an upper pulse-operated electric stepping motor 40 and a lower pulse-operated electric stepping motor 41.

The motor 40 has a shaft 42 with a driving pinion 43 which meshes with the larger part of a double pinion 44. The smaller part of the double pinion 44 meshes with an upper gear wheel 45 of a differential gear 46.

In an exactly similar manner, the lower motor 41 has a shaft 47 with a pinion 48 meshing with a double pinion 49 which in turn meshes with a lower gear wheel 50 of the differential gear 46.

The pinions 44 and 49 are rotatably mounted by needle bearings on a fixed shaft 51 and the gear wheels 45 and 50 are mounted on the rotor shaft 31 by means of bearings 52 and 53 respectively. The gear wheels 45 and 50 have bevel gear portions 54 and 55 respectively and these mesh with two planetary bevel pinions 56 and 57. The pinions 56 and 57 are rotatably mounted on stub shafts 58 and 59 which are fixed to and project radially from the pinion shaft 31.

It will thus be seen from the known mechanics of differential gears, that when the two stepping motors 40 and 41 are rotated at equal speeds, but in opposite directions by the delivery of pulses of equal frequencies which are in phase with each other, the wheels 45 and 50 will be rotated at equal speeds, but in opposite directions and the planet pinions 56 and 57 will also be rotated at equal speeds and in opposite directions, but they will only rotate about the axes of their stub shafts 58 and 59 and these stub shafts will themselves remain stationary. Accordingly the rotor shaft 31 will not be rotated.

If, however, one of the motors 40 or 41 is stopped, the planetary pinions 56 and 57 will move around the stationary one of the two gear wheels 45 and 50, that is to say the planetary pinions will orbit and the rotor shaft 31 and with it the rotor 27 will be rotated.

The rotor 27 can similarly be rotated, but at a lower speed merely by rotating one of the motors 40 or 41 faster than the other. What is more, by first rotating the motor 40 faster than the motor 41, the rotor 27 will be rotated in one direction and then by rotating the motor 41 faster than the motor 40, the rotor 27 will be rotated in an opposite direction. Thus by varying the speed of rotation of the motors 40 and 41, but without stopping either of these motors, the rotor 27 can be rotated continuously in either direction or it may be oscillated to and fro with any required frequency and speed solely in dependence upon the frequency of the pulses delivered to the motors 40 and 41.

When the rotor 27 is rotated, a torque will be applied to it, and there will accordingly be a reverse torque on the pivotally mounted gearbox 36. Rotation of the gearbox 36 is prevented by a load cell 60 (see FIG. 1) which is attached to it and which is connected by a rod 61 to a bracket 62 which is fixed to the fixed plate 11.

As shown in FIGS. 4 to 6, the upper end of the rod 17 has a peripheral groove 63 which forms one part of a catch. The upper platen 21 and the cover 22 which is attached to the platen 21 by a bracket 64, are acted upon by a gas strut 65 which counterbalances the platen 21 and the parts which it carries about its pivot 66 and also by a small pneumatic cylinder 67.

A second catch part 68 containing a socket for receiving the upper end of the rod 17 and a small pneumatic ram, which is not shown, are fixed to the underside of the upper platen 21 and with the rods 17–19 raised by the pneumatic cylinder 9 acting through the cross head 20, and the pneumatic cylinder 67 extended, the platen 21 assumes the raised position shown in FIG. 4. This provides easy access to the chamber 26 in the lower die 25. With this easy access, the rotor with its spindle 28 can be lifted out of the socket in the upper end of the shaft 31 and the chamber 26 can be cleaned. In the customary way with rheometers of the kind with which the present invention is concerned, part of a sample to be tested is then inserted into the chamber 26 and the rotor 27 is then replaced in position. A further part of the sample to be tested is then placed over the rotor 27 and after this has been done, the pneumatic cylinder 67 is retracted to turn the upper platen 21 and the parts which it carries about the pivot 66 into the position shown in FIG. 5. At this stage the catch in the part 68 is caused to engage by its pneumatic ram in the groove at the upper end of the rod 17. At this stage the chamber 26 is still open, but the upper die 24 is situated immediately above the lower die 25. Next the pneumatic cylinder 9 is operated to retract its piston rod 10 and lower the cross head 20, which in turn pulls the rods 17 to 19 downwards and this pulls the upper platen 21 downwards to compress the sample to be tested in the chamber 26 and close the chamber completely.

The pneumatic cylinders 9 and 67 and the pneumatic cylinder which operates the catch 68 are supplied with compressed air from a supply, which is not shown, under the control of solenoid valves which are also not shown. These solenoid valves together with the motors 40 and 41 are in turn controlled by an electronic controller 69, which is indicated in FIG. 1. The controller 69 contains conventional electronic circuitry and this circuitry includes circuits for controlling the solenoid valves which operate the various pneumatic cylinders, pulsing circuits for energising the motors 40 and 41 and in addition a circuit with a digital read out which indicates via the load cell 60, the torque which acts upon the gearbox 36 and thus also the torque acting upon the rotor 27. The controller 69 also contains a timing device which is connected to the circuits of the motors 40 and 41 and the circuit of the load cell 60 so that the time between any movements of the rotor 27 as provided by the motors 40 and 41 and the instants of zero or maximum torque as indicated by the load cell 60 can be measured.

By means of the differential mechanical drive of the rotor 27 through the differential gear 46 and under the operation of the pulse-operated stepping motors 40 and 41 under the control of the controller 69 as already described, it is possible to carry out very varied and versatile tests upon samples of rubber or synthetic elastomers placed in the chamber 26 during the course of vulcanisation or curing. To enable continuous testing to be carried out as vulcanisation or curing proceeds, both the dies 24 and 25 are provided with electrical heating devices which are not shown. These may or may not be used as required.

In one particular test for which the rheometer in accordance with the invention is particularly intended, a sample of rubber or of a synthetic elastomer is inserted into and held under pressure in, the chamber 27 in the manner already described. The sample is then subjected to a substantial angular shearing strain by rotating the rotor 27 through an angle which is greater than the total angle of recovery of the sample when the torque applied to it through the rotor 27 is released. This angular shearing strain is applied by rotating the rotor 27 by operation of either one or both of the motors 40 and 41. The angle of rotation of the rotor 27 is indicated by an indicator on the controller 69 in dependence upon the number of pulses applied to either one or both of the motors.

The rotation of the rotor 27 is then stopped and this may be done by stopping both of the motors 40 and 41, but it is preferably done by continuing to rotate both the motors, but at identical speeds and in opposite directions to each other. The rotor is then rotated in a reverse direction by one step through a predetermined angle by the application to one motor of a single pulse or predetermined number of pulses greater than the number of pulses applied to the other motor. In this example this step is equal to 1.8 minutes of arc. As the reverse rotation takes place, there will be a momentary torque exerted by the sample on the rotor in the forward direction and this is indicated by the controller through the load cell 60. As recovery of the sample takes place, however, a torque in the reverse direction will build up on the rotor 27 and this is again indicated by the controller and is recorded. Reverse rotation of the rotor 27 takes place in successive steps and at each step the initial forward torque and then the reverse torque on the rotor 27 is observed and recorded. This continues until the reverse torque on the rotor after a step of reverse rotation of the rotor 27 has taken place is zero. The total reverse rotation of the rotor 27 is then indicated by the controller in dependence upon the total number of pulses applied to produce the reverse rotation. This total angle of reverse rotation indicates the total angle of recovery of the sample in the chamber 26.

After each step of reverse rotation of the rotor, the time taken for the torque applied to the rotor by the sample to fall to zero and then to increase to a maximum in the reverse direction is measured by the timing device in the controller.

Preferably, in order to compensate for any back-lash that there may be in the driving mechanism, after the last step of reverse rotation of the rotor has taken place after which the reverse torque on the rotor has fallen to zero, the rotor is again rotated in a forward direction through one or more steps until a minimum observable torque upon the rotor by the sample is again indicated by the load cell. When this is done, the angle of recovery of the sample is taken as the mean angle between that after the last step of reverse rotation of the rotor has taken place and that after the forward rotation has taken until the minimum observable torque is indicated.

This testing technique may be repeated time after time as the sample, which may be initially completely uncured or unvulcanised, is cured or vulcanised by heating the dies 24 and 25.

This example of the rheometer in accordance with the invention has the further great advantage that in addition to being able to carry out the testing method just described, it can also be used to carry out tests similar to those made by the well-known Mooney Viscometer by continuously rotating the rotor in one direction and measuring gradually increasing torque required to produce this rotation. It may also be used to carry out tests which have in the past been made by the conventional type of oscillating disc rheometer as described in GB-A No. 1036904. What is more the rheometer in accordance with the invention has the advantage over the conventional oscillating disc rheometer that the angle through which the rotor is oscillated may be varied during the course of the test by varying the speeds of rotation of the two motors 40 and 41. Thus the sample may be subjected to large angles of strain at the start of its test and the angles of strain can be progressively reduced as the sample is vulcanised or cured. Variation of the angle of oscillation during the course of a test is not possible with a rheometer as described in GB-A No. 1036904. The variation of the angle of oscillation of the rotor during the course of the test gives more accurate test results during the stage of testing while the sample is viscous than those that can be obtained with a conventional oscillating disc rheometer since the conventional oscillating disc rheometer must have its oscillation set at an amplitude which is applicable to the sample when in its cured state and this amplitude is too small for accuracy when the sample is in its viscous state.

Figure 7:
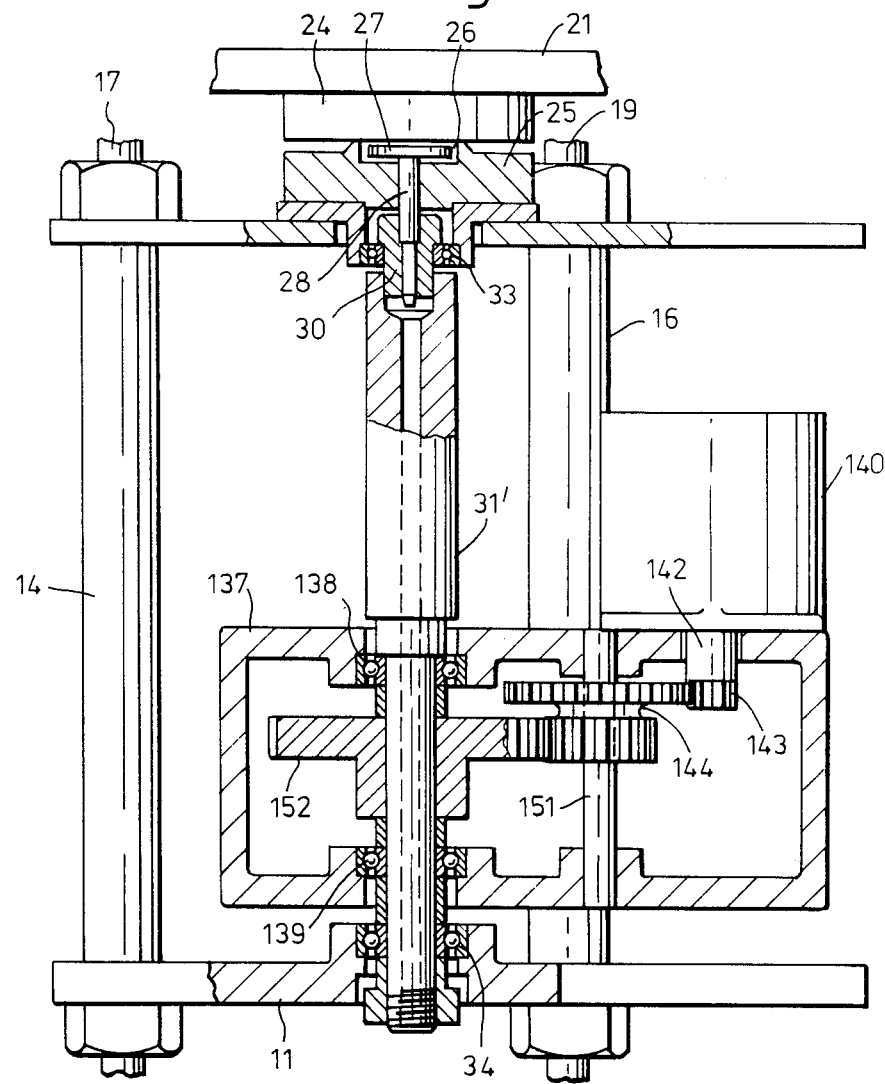
FIG. 7 is a view similar to FIG. 2, but showing a modification of the drive of the rotor.

The rheometer illustrated in FIG. 7 of the drawings is constructed and can be operated in very much the same way as the first example described with reference to FIGS. 1 to 6 of the drawings, but in place of the gearbox 36 with its differential gear 46 and two pulse-operated stepping motors 40 and 41, the example shown in FIG. 7 is provided with a simplified drive. This comprises a gearbox 137 which is rotatably mounted on the shaft 31' by means of bearings 138 and 139. The gearbox 137 carries a single reversible pulse-operated stepping motor 140 which has a driving shaft 142 with a pinion 143. The pinion 143 meshes with the larger part of a double pinion 144 which is rotataby mounted on a shaft 151. The smaller part of the double pinion 144 meshes with a gear wheel 152 which is permanently keyed to the rotor shaft 31'.

By means of this drive, the rotor 27 may be rotated step by step in one direction or in a reverse direction or it may be oscillated as in the first example, but there different modes of driving can only be effected by stopping and starting the motor 140. This is not so efficient as the drive in the first example with the two separate stepping motors which drive the shaft 31 through a differential gear because pulse-operated stepping motors have considerably starting inertia and, what is more, when oscillation of the shaft 31' is taking place, only parts of the peripheries of the pinions 144 and 152 are in use and in consequence these pinions are liable to suffer over a period of time from uneven wear which can upset the accuracy of the rheometer.

I claim:

1. In a rheometer which includes means defining a chamber for holding a sample of material of which the properties are to be measured under pressure in said chamber, a rotor, said rotor including a surface in contact with said sample in said chamber, drive means for rotating said rotor, and torque measuring means for measuring torque applied to said rotor as it is rotated, the improvements comprising: said drive means being reversible, and including a pulse-operated electric stepping motor, gearing connecting said motor to said rotor, and circuit means for supplying electrical pulses to said motor to rotate said motor and thereby rotate said rotor, said drive means enabling said rotor to be rotated selectively in either direction in steps of not more than 20 minutes of arc.

2. A rheometer as claimed in claim 1, in which said rotor is a disc, and further comprising means rotatably mounting said disc in said chamber in a position in which, in use, said disc is entirely surrounded by said sample.

3. A rheometer as claimed in claim 1, further comprising timing means operatively connected in said drive means, said timing means indicating the time taken for variations in the torque on said rotor to take place after said rotor has been rotated by said drive means.

4. A rheometer as claimed in claim 1, in which said motor and said gearing enable said rotor to be rotated in steps of 1.8 minutes of arc or less.

5. A rheometer as claimed in claim 1, in which said drive means incorporates means for selectively rotating said rotor step by step in one direction, step by step in a reverse direction and oscillating said rotor step by step by rotating said rotor through one or more steps in said one direction followed by rotation of said rotor through one or more steps in said opposite direction.

6. A rheometer as claimed in claim 5, in which said drive means includes first and second pulse-operated electric stepping motors, said circuit means includes means for supplying pulses selectively to said first and second motors and said gearing includes differential gearing means.

7. A rheometer as claimed in claim 1, in which said drive means includes only a single pulse-operated electric stepping motor, said single motor being reversible.

8. A rheometer as claimed in claim 1, in which said motor and said gearing are constructed as a unit, said unit having an output shaft connecting said bearing to said rotor, and further comprising means freely rotatably mounting said unit, a load cell forming said torque measuring means and means connecting said load cell to said unit to prevent rotation of said unit, whereby said load cell indicates a reaction torque on said unit when said rotor is being rotated and said load cell hence indicates the torque on said rotor.

9. A rheometer as claimed in claim 1, further comprising a housing, said housing including first and second parts which are separable from each other along a plane transverse to the axis of rotation of said rotor, said first and second parts enclosing said chamber there between, and further comprising a mechanism for clamping said parts of said housing together and for moving said part of said housing on the side of said plane remote from said drive means linearly away from said plane and tilting said part to provide access to said chamber and to said rotor for insertion and removal of said sample into and from said chamber.

10. In a method of measuring the recovery of a sample of rubber or of a synthetic elastomer, said method comprising the steps of inserting said sample under pressure into the chamber of a rheometer which includes a rotor which has a surface in contact with said sample in said chamber and has drive means by which it is rotatable and torque measuring means for measuring the torque applied to said rotor as it is rotated; rotating said rotor in one direction to apply a substantial angular shear strain to said sample, said angular shear strain being greater than the maximum angular recovery of said sample; stopping the rotation of said rotor in said one direction; rotating said rotor in a reverse direction step by step through predetermined angles; observing the torque, as indicated by said torque measuring means, applied to said rotor by said sample as said sample recovers after each step of said reverse rotation; and then rotating said rotor through a further step until said observed torque falls to zero at which time the reverse rotation of said rotor indicates the angular recovery of said sample.

11. A method as claimed in claim 10, further comprising the step of measuring the time taken after each step of reverse rotation of said rotor for the torque on said rotor to increase to a maximum in said reverse direction or to fall to zero after said last step of reverse rotation has taken place.

12. A method as claimed in claim 11, further comprising a step of again rotating said rotor in said one direction through one or more steps after said last step of reverse rotation has taken place and said observed torque has fallen to zero, said rotation in said one direction being continued until a minimum observable torque in said reverse direction is indicated by said torque measuring means.

* * * * *